United States Patent [19]

Fulton, Jr.

[11] 4,350,681

[45] * Sep. 21, 1982

[54] STABILIZED BENZOYL PEROXIDE COMPOSITIONS

[75] Inventor: James E. Fulton, Jr., Key Biscayne, Fla.

[73] Assignee: A.H.C. Pharmacal, Inc., Miami, Fla.

[*] Notice: The portion of the term of this patent subsequent to Feb. 19, 1997, has been disclaimed.

[21] Appl. No.: 104,629

[22] Filed: Dec. 17, 1979

Related U.S. Application Data

[63] Continuation-in-part of Ser. No. 840,339, Oct. 7, 1977, Pat. No. 4,189,501.

[51] Int. Cl.$^3$ .................. A61K 7/20; A61K 31/075
[52] U.S. Cl. ............................. 424/53; 424/338
[58] Field of Search ........................ 424/338, 53

[56] References Cited

U.S. PATENT DOCUMENTS

| | | | |
|---|---|---|---|
| 2,216,485 | 10/1940 | Brandt | 424/56 X |
| 2,317,297 | 4/1943 | Omohundro et al. | 424/53 |
| 2,501,145 | 3/1950 | Smith | 424/53 |
| 3,535,422 | 10/1970 | Cox et al. | 424/164 |
| 4,056,611 | 11/1977 | Young | 424/62 |
| 4,189,501 | 2/1980 | Fulton | 424/338 |

OTHER PUBLICATIONS

Handbook of Non-Prescription Drugs, 5th Ed., 1–1977, pp. 314 and 317–323.

*Primary Examiner*—Leonard Schenkman
*Attorney, Agent, or Firm*—Blum, Kaplan, Friedman, Silberman & Beran

[57] ABSTRACT

Benzoyl peroxide dispersed in an aqueous medium is stabilized by the presence of glycerol. Where the composition includes a finely dispersed and mild abrasive, together with a wetting agent and a thickener, the composition is suitable for use as a toothpaste. Where the composition includes a suitably large quantity of wetting agent and an appropriate soft abrasive, the composition is effective as a body scrub in preparation for surgery.

13 Claims, 1 Drawing Figure

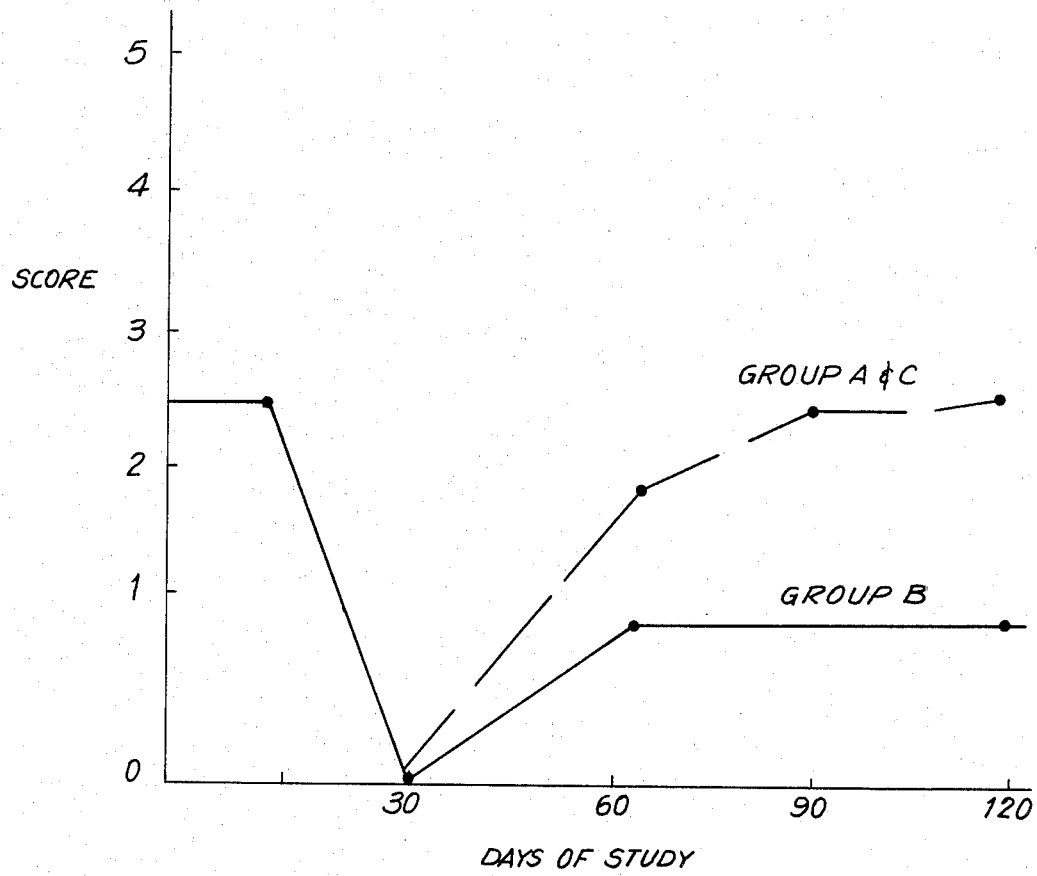

STABILIZED BENZOYL PEROXIDE COMPOSITIONS

CROSS-REFERENCE TO RELATED APPLICATIONS

The present application is a continuation-in-part of my earlier application "Composition and Method for the Treatment of Acne" filed Oct. 7, 1977, and having the Ser. No. 840,339. Said earlier application has matured as U.S. Pat. No. 4,189,501 and the material therein is incorporated herein by reference as if fully presented.

The subject matter of the present application is also related to my co-pending application Ser. No. 104,630 bearing the same title as the parent application and filed on the same date as the present application.

BACKGROUND OF THE INVENTION

As disclosed in the aforenoted parent application, glycerol stabilizes organic peroxides dispersed in an aqueous medium. The quantity of peroxide can vary from about 1% to about 30% by weight and the quantity of glycerol can vary from about 5 volume % to about 50 volume %. When combined with suitable thickener and alkali to bring the pH to a value between 3.5 and 5.0, the composition is effective in the treatment of acne when applied topically.

The effect of glycerol on the decomposition rate of organic peroxides was unexpected since monohydric alcohols and glycols by themselves do not stabilize the benzoyl peroxide.

The present invention is concerned with benzoyl peroxide compositions useful for purposes other than the treatment of acne where the benzoyl peroxide is also stabilized by glycerol.

SUMMARY OF THE INVENTION

Compositions containing from 1 to 30 weight % of benzoyl peroxide, and 5 to 50 volume % of glycerol in an aqueous medium are useful as a toothpaste and as a body scrub in preparation for surgery. Where the composition contains a pharmaceutically-acceptable wetting agent and a finely dispersed abrasive together with a thickener, the composition is effective for the removal of plaque from teeth. Where the composition contains a substantially greater content of wetting agent and granular polyethylene as abrasive, the composition is suitable for a body scrub.

Accordingly, an object of the present invention is a composition containing benzoyl peroxide and sufficient glycerol to stabilize said benzoyl peroxide, in an aqueous medium.

Another object of the present invention is a composition containing benzoyl peroxide, glycerol for stabilizing said benzoyl peroxide, and a thickener and mild abrasive in sufficient quantities so that said composition is a paste, said composition being useful as a toothpaste.

A further object of the present invention is a composition comprising benzoyl peroxide and glycerol for stabilizing same, said composition containing a substantial quantity of a wetting agent and an extremely mild abrasive, such a composition being suitable as a body scrub in preparation for surgery.

Still other objects and advantages of the invention will in part be obvious and will in part be apparent from the specification.

The invention accordingly comprises a composition of matter possessing the characteristics, properties, and the relation of constituents which will be exemplified in the composition hereinafter described, and the scope of the invention will be indicated in the claims.

BRIEF DESCRIPTION OF THE DRAWING

For a fuller understanding of the invention, reference is had to the following description taken in connection with the accompanying drawing, in which:

The single FIGURE shows the effect of a toothpaste in accordance with the present invention on plaque index, in comparison with toothpaste formulations which do not contain benzoyl peroxide.

It is also to be understood that the following claims are intended to cover all of the generic and specific features of the invention herein described and all statements of the scope of the invention which, as a matter of language, might be said to fall therebetween.

DESCRIPTION OF THE PREFERRED EMBODIMENTS

Aqueous compositions containing from 1 to 30 weight % of benzoyl peroxide are stabilized by the incorporation of from 5 to 50 volume % of glycerol. The most useful compositions so far as toothpastes and body scrubs are concerned contain from 1 to 5 weight % of benzoyl peroxide and from 12 to 30 volume % of glycerol. Where the composition is to be used as a toothpaste, the benzoyl peroxide content should be from about 1.2 to about 1.8 weight % and the glycerol content should be from about 20 to about 30 volume %. In addition, the composition should contain from 25 to 35 weight % of a mild abrasive and from 1 to about 3.5 volume % of a wetting agent. The preferred thickener is carboxyvinyl polymer having a molecular weight of about 4,000,000 and sold under the name of Carbopol 940 by B. F. Goodrich. The preferred wetting agent is sodium lauryl sulfonate. Optionally, up to about 0.7 weight % of sodium saccharin may be added as a sweetener and up to about 1 weight % of flavor. Also, up to about 0.05 weight % of coloring material such as a dye may be added. Following are three toothpaste compositions exemplifying the present invention.

| Formula | #1 | #2 | #3 |
|---|---|---|---|
| Water | q.s. | q.s. | q.s. |
| Glycerin | 25% | 25% | 25% |
| Dicalcium Phosphate | 30% | 30% | 30% |
| Sodium Lauryl Sulfate | 2% | 2.5% | 2.5% |
| Benzoyl Peroxide | 1.5% | 1.5% | 2.5% |
| Sodium Saccharin | 0.15% | 0.4% | 0.4% |
| Carboxyvinyl Polymer | 2.5% | 6.0% | 6.0% |
| D & C Red #36 | 0.01% | 0.01% | 0.01% |
| Flavor | 0.47% | 0.75% | 0.75% |

Quantities of glycerol and sodium lauryl sulfonate in volume %. All other quantities in weight %.

The efficacy of benzoyl peroxide toothpaste, formulation No. 3, for the reduction of dental plaques and gingivitis was investigated, the Standard Plaque Index (PL I) and Gingival Inflammation Index (G I) being determined during a double-blind randomized comparison of:

(A) Non-antibacterial toothpaste (Crest).
(B) Toothpaste formulation No. 3.
(C) Formulation No. 3 but minus benzoyl peroxide.

The test was run on 36 adult male and female volunteers, minimum criteria for selection into the study requiring at least 16 healthy teeth without severe peridontal disease and absence of diabetes. None of the subjects were receiving antibiotic therapy or, in the case of females, were on oral contraceptives.

On Day No. 1 of the 30-day pre-test period, all of the subjects were evaluated by the tooth surface stain scoring system using the labial surface of the 16 most anterior teeth. This involved both an area score and an intensity score developed after rinsing the mouth with disclosing solution. Following is the basis for the area score.

| AREA SCORE |
| --- |
| 0 - No Stain |
| 1 - Specks of plaque at gingival margin |
| 2 - Continuous line of plaque at gingival margin |
| 3 - Plaque on gingival ⅓ of tooth surface |
| 4 - Plaque on gingival ⅔ of tooth surface |
| 5 - Plaque on more than ⅔ of tooth surface |

The gingival status was monitored as to color, presence of edema, altered contour or bleeding on probing.

| GINGIVAL SCORE |
| --- |
| 0 - Normal Gum |
| 1 - Mild inflammation with reddish discoloration |
| 2 - Mild inflammation with reddish discoloration, mild edema and bleeding on probing |
| 3 - Moderate inflammation with violaceous discoloration, edema and altered contour |
| 4 - Same as 3 but with additional bleeding on probing |

Following evaluation on Day No. 1 of the study, patients were given a soft toothbrush and a non-antibacterial toothpaste and instructed to brush their teeth twice daily. The subjects were told to refrain from brushing their teeth on the morning of the 14th and 30th days to permit reevaluation. Those subjects with a stable score (30 subjects) were continued to Phase II. On Day No. 30 of the pre-test period (Phase II) the teeth of all participants were scaled and polished and the participants were again given toothbrushing instructions.

Phase II

The 30 remaining volunteers were randomly assigned to one of three groups (A), (B) and (C), and were given the appropriate toothpaste. The participants were instructed not to brush on Day No. 60, 90 or 120 of the study. On these days, the PL I and G I were again evaluated. The dental plaque score is shown in the FIGURE. As can be seen from the FIGURE, the participants initially had an average plaque index of about 2.5. After scaling, the plaque index reached almost to the initial level for Groups (A) and (C) in 60 days and then up to the initial level in 90 days.

In contrast, the plaque index for the groups which had been brushing with the 2.5 weight % benzoyl peroxide toothpaste had a plaque index which was below 1. Since the members of Group (C) were tested with the toothpaste of the same composition as the members of Group (B) except for the benzoyl peroxide, it is evident that it is the benzoyl peroxide which is effective in lowering the plaque index. Moreover, after scaling, the gingival index also increased gradually in test Groups (A) and (C) but not in test Group (B). Also, the preparation is effective in eliminating gingival inflammation as none of the subjects in Group (B) showed gingival bleeding on probing.

| GINGIVAL INDEX | |
| --- | --- |
| GROUP | INDEX |
| A | 2.1 |
| B | 1.0 |
| C | 2.5 |

With respect to body scrub solutions, these are conventionally used for "scrubbing-up" prior to surgery. Such solutions are used on the hands and arms of the surgeons who are about to participate in a surgical procedure and on the body of the subject. Compositions to be used as body scrubs comprise from 2 to 4 weight % of benzoyl peroxide, from 12 to 18 volume % of glycerol, up to 8 volume % of propylene glycol, from 1 to 4 weight % of thickener, from 12 to 20 volume % of wetting agent, and from 0.20 to 0.28 weight % of alkali in an aqueous medium. The preferred wetting agent is a solution consisting essentially of 3 parts of ammonium lauryl sulfonate and 1 part of long chain imidazoline zwitterion. Also, the composition may contain up to 0.05 weight % of dye as coloring material, up to 1.5 weight % of ground mica for luster, up to 0.1% of perfume oil and up to 15 weight % of microthene (granular polyethylene) for abrasion. Following is a sample composition:

| STABILIZED BENZOYL PEROXIDE SURGICAL SCRUB | |
| --- | --- |
| Percent | Ingredient |
| 3.5 | Benzoyl Peroxide 78% |
| 14.8 | Glycerin |
| 6.0 | Propylene Glycol |
| 0.025 | D & C Red #36 |
| 1.2 | Carbopol 940 (carboxyvinyl polymer) |
| 12.0 | Ammonium Lauryl Sulfate |
| 4.0 | Long Chain Imidazoline Zwitterion |
| 1.0 | Pearl White Ground Mica |
| 0.24 | Sodium Hydroxide |
| 0.05 | Perfume Oil |
| 10.0 | Microthene MA 778 Polyethylene Beads |
| 47.16 | Purified Water |

NOTE:
Liquid content in volume % (1 ml taken as 1 gram)
Solids content in weight %

In both the toothpaste and the surgical scrub the quantity of alkali used is such as to bring the pH of the composition to from 3.5 to 5.0.

The Standard Glove-Juice test was employed in a double-blind comparison to determine the efficacy of the surgical scrub. The materials tested were:

A. Non-antibacterial soap (Ivory)
B. Surgical Scrub with 2.5 weight % Benzoyl Peroxide
C. Surgical Scrub without Benzoyl Peroxide
D. Phisohex Twenty-four (24) adult male and female volunteers were selected for the test, one criterion for selection into the study being a bacterial count of $1.5$–$2.0 \times 10^4$ per hand. In addition, individuals receiving antibiotic therapy or in the case of females on oral contraceptives, were excluded from the test.

On Day No. 1 of a two-week pre-test period all subjects were instructed to use Ivory Soap and to avoid products containing anti-microbials. Subjects were also given rubber gloves to be worn during their normal daily routines to avoid contamination with germicidal agents.

The baseline period for the study was the week following the two weeks of pre-conditioning. Baseline counts were performed three times during this period. In preparation for the counts, the hands were washed for thirty seconds with Ivory Soap, the washing extending ⅔ of the distance from wrist to elbow. Excess water was shaken from the hands and standard gloves were donned over the wet hands. Stripping solution was added to the gloves and the hands were massaged through the gloves for one minute. An aliquot was withdrawn from each glove and a bacterial count carried out.

During the test period, both hands were scrubbed for six minutes and placed in sterile surgical gloves. One hand was immediately removed and stripping solution was added to the glove and the hand immediately rinsed with the solution; plate counts were performed at this time. The other hand was incubated in a glove for one, two, four and six hours. Stripping solution was added and plated. A different subject was used for each time period indicated.

The stripping solution is a mixture of the detergent Triton X-100 at a concentration of 0.1% in the bacterial transfer medium called "Eugon's Broth". This material is injected into the surgical glove, massaged around the fingernails particularly, and then pipetted out. After dilution, it is applied to a plate.

During the two-week pre-test period it was found that all subjects had stable counts. During the test period both hands were scrubbed with the solutions A, B, C or D. As a further refinement of the procedure, the 24 volunteers were broken into four groups of 6 volunteers per group. It was found that the surgical scrub containing benzoyl peroxide was highly effective in reducing the bacteria count in the subjects tested, the test results clearly showing that the count remained low over the entire period of six hours. Further, the Ivory Soap test in Group A and the surgical scrub without benzoyl peroxide for Group C were relatively ineffective in reducing the bacterial count. Phisohex was found to be approximately half as effective as the surgical scrub with the benzoyl peroxide.

As will be evident to those skilled in the art, a wide variety of wetting agents, thickeners and abrasives may be used in formulating both the toothpaste compositions and the surgical scrub compositions. In general, higher levels of benzoyl peroxide require higher levels of glycerol for effective stabilization and the quantity of thickener can be adjusted in accordance with the amount of abrasive to achieve appropriate viscosities for toothpaste on the one hand and for a surgical scrub on the other.

As noted in my application having the Ser. No. 840,339, said application being incorporated herein by reference as if fully published, other suitable thickeners are magnesium aluminum silicate and finally divided silica. In general, in preparing formulations in accordance with the present invention, the benzoyl peroxide is added to the vehicle in a high-shear blender and agitated for several minutes until dispersion is complete and the product is uniform. The thickener is added to a small quantity of the vehicle and the resultant solution or dispersion is added to the benzoyl peroxide dispersion. Agitation is continued until the product is smooth, after which alkali, preferably in the form of a dilute solution, is added, blending same until the resultant gel or solution is homogenous.

It will thus be seen that the objects set forth above, among those made apparent from the preceding description, are efficiently attained and, since certain changes made be made in the above composition of matter without departing from the spirit and scope of the invention, it is intended that all matter contained in the above description shall be interpreted as illustrative and not in a limiting sense.

What is claimed is:

1. A stabilized benzoyl peroxide composition, comprising from 1 to 30 weight % of benzoyl peroxide, from 5 to 50 volume % of glycerol and from 25 to 35 weight % of a mild abrasive in an aqueous medium, said composition being useful in toothpastes and as a body scrub.

2. A stabilized benzoyl peroxide composition, as claimed in claim 1, wherein said composition comprises from 1 weight % to 5 weight % of benzoyl peroxide and from 12 to 30 volume % of glycerol, said composition being useful in toothpastes and as a body scrub.

3. A stabilized benzoyl peroxide composition as claimed in claim 1 wherein the abrasive is finely dispersed and wherein the composition further contains a pharmaceutically acceptable wetting agent and thickener; said abrasive, wetting agent and thickener being present in quantities such that said composition is effective for removing plaque from teeth.

4. A stabilized benzoyl peroxide composition, as claimed in claim 3, wherein said composition comprises from 1.2 to 1.8 weight % benzoyl peroxide, from 20 to 30 volume % of glycerol, from 1 to 10% of thickener, from 25 to 35 weight % of a mild abrasive, and from 1 to 3.5 volume % of wetting agent, said composition being useful as a toothpaste.

5. A stabilized benzoyl peroxide composition, as claimed in claim 4, wherein said abrasive is dicalcium phosphate, said composition being useful as a toothpaste.

6. A stabilized benzoyl peroxide composition, as claimed in claim 4, wherein said wetting agent is sodium lauryl sulfonate, said composition being useful as a toothpaste.

7. A stabilized benzoyl peroxide composition as claimed in claim 4, wherein said thickener is carboxyvinyl polymer.

8. A stabilized benzoyl peroxide composition as claimed in claims 4, 5 or 6, wherein said composition contains up to about 0.7 weight % of sodium saccharin as sweetener, up to about 1 weight % of flavor and up to about 0.05 weight % of coloring material, said composition being useful as a toothpaste.

9. A stabilized benzoyl peroxide composition as claimed in claim 1, wherein said composition comprises from 2 to 4 weight % of benzoyl peroxide, from 12 to 18 volume % of glycerol, up to 8 volume % of propylene glycol, from 1 to 4 weight % of thickener, from 12 to 20 volume % of wetting agent, and from 0.20 to 0.28 weight % of alkali in an aqueous medium, said composition being useful as a body scrub.

10. A stabilized benzoyl peroxide composition as claimed in claim 9, wherein said wetting agent consists essentially of 3 parts of ammonium lauryl sulfonate and one part of long chain imidazoline zwitterion.

11. A stabilized benzoyl peroxide composition as claimed in claim 9, wherein said thickener is carboxyvinyl polymer.

12. A stabilized benzoyl peroxide composition as claimed in claim 9, wherein said alkali is sodium hydroxide.

13. A stabilized benzoyl peroxide composition as claimed in claims 9, 10, 11 or 12, wherein said composition further comprises up to 0.05 weight % of dye as coloring material, up to 1.5 weight % of ground mica for luster, up to 0.1% of perfume oil and up to 15 weight % of microthene for abrasion.

* * * * *